US008889213B2

(12) United States Patent
Samburski et al.

(10) Patent No.: US 8,889,213 B2
(45) Date of Patent: Nov. 18, 2014

(54) PROCESSES FOR COATING A CARRIER WITH MICROPARTICLES

(75) Inventors: Guy Samburski, Ganot Hadar (IL); Ziv Kurgan, Har Adar (IL); Abed Masarwa, Karem El-Jebaly (IL); Akper Sadykhov, Kiryat Mozkin (IL)

(73) Assignee: Teva Pharmaceutical Industries Ltd., Petach-Tikva (IL)

(*) Notice: Subject to any disclaimer, the term of this patent is extended or adjusted under 35 U.S.C. 154(b) by 610 days.

(21) Appl. No.: 12/693,602

(22) Filed: Jan. 26, 2010

(65) Prior Publication Data

US 2010/0189878 A1 Jul. 29, 2010

Related U.S. Application Data

(60) Provisional application No. 61/147,287, filed on Jan. 26, 2009.

(51) Int. Cl.
| *B05D 3/00* | (2006.01) |
| *B05D 1/12* | (2006.01) |
| *B01J 8/24* | (2006.01) |
| *A61K 9/28* | (2006.01) |
| *A61K 9/50* | (2006.01) |

(52) U.S. Cl.
CPC .............. *A61K 9/5078* (2013.01); *A61K 9/5089* (2013.01)
USPC .......... 427/2.15; 427/180; 427/185; 424/427; 424/489; 424/490

(58) Field of Classification Search
USPC ............... 427/2.14, 2.24, 2.25; 424/474, 490, 424/489, 463
See application file for complete search history.

(56) References Cited

U.S. PATENT DOCUMENTS

| 2,648,609 | A | | 8/1953 | Wurster |
| 2,799,241 | A | | 7/1957 | Wurster |
| 3,089,824 | A | | 5/1963 | Wurster |
| 3,196,827 | A | | 7/1965 | Wurster |
| 3,207,824 | A | | 9/1965 | Wurster |
| 3,253,944 | A | | 5/1966 | Wurster |
| 5,833,891 | A | * | 11/1998 | Subramaniam et al. .......... 264/7 |
| 6,899,322 | B2 | | 5/2005 | Sadykhov |
| 6,926,908 | B2 | | 8/2005 | Robinson et al. |

(Continued)

FOREIGN PATENT DOCUMENTS

| CA | 2136704 | 5/1995 |
| CA | 2 669 009 | 5/2008 |

(Continued)

OTHER PUBLICATIONS

Krober et al. Supercritical Antisolvent precipitation atomization and product quality. Proceedings of the 6th International Symposium on Supercritical fluids, Tome 3, Vesailles, France, Apr. 2003, pp. 1641-1646.*

(Continued)

*Primary Examiner* — Cachet Sellman
(74) *Attorney, Agent, or Firm* — RatnerPrestia

(57) ABSTRACT

Processes for coating a carrier with microparticles of a drug are described. For example, a coated carrier can be obtained in a one-stage process that entails evaporating a solvent from microdroplets of a solution containing an API to obtain dry microparticles, which are then coated on the carrier.

25 Claims, 1 Drawing Sheet

(56) References Cited

U.S. PATENT DOCUMENTS

| | | | |
|---|---|---|---|
| 2002/0071871 A1* | 6/2002 | Snyder et al. | 424/489 |
| 2002/0132011 A1 | 9/2002 | Gordon et al. | |
| 2003/0066800 A1* | 4/2003 | Saim et al. | 210/634 |
| 2006/0228487 A1 | 10/2006 | Schaible et al. | |
| 2007/0141161 A1* | 6/2007 | Shaw et al. | 424/489 |
| 2010/0143331 A1 | 6/2010 | Schultz-Fademrecht et al. | |

FOREIGN PATENT DOCUMENTS

| | | |
|---|---|---|
| EP | 0 706 794 | 4/1996 |
| WO | WO 95/23613 | 9/1995 |
| WO | WO 95/24183 | 9/1995 |
| WO | WO 97/35562 | 10/1997 |
| WO | WO 01/45674 | 6/2001 |
| WO | WO 03/082247 | 10/2003 |
| WO | WO 2007/001957 | 1/2007 |
| WO | WO 2007039417 A1 | 4/2007 |
| WO | WO 2007/117661 | 10/2007 |
| WO | WO-2008/055951 A1 | 3/2008 |

OTHER PUBLICATIONS

Mukhopadhyay et al. Mass and heat Transfer analysis of SAS: effects of thermodynamic states and flow rates on droplet size. J. of Supercritical fluids. vol. 30. (2004) pp. 333-348.*

Ultra Sonic Atomizer, http://www.sonozap.com/Ultrasonic_Atomizer.html (Oct. 5, 2008).

Japanese Final Office Action with English translation, JP 2011-548201, dated May 2, 2014 (5pp.).

* cited by examiner

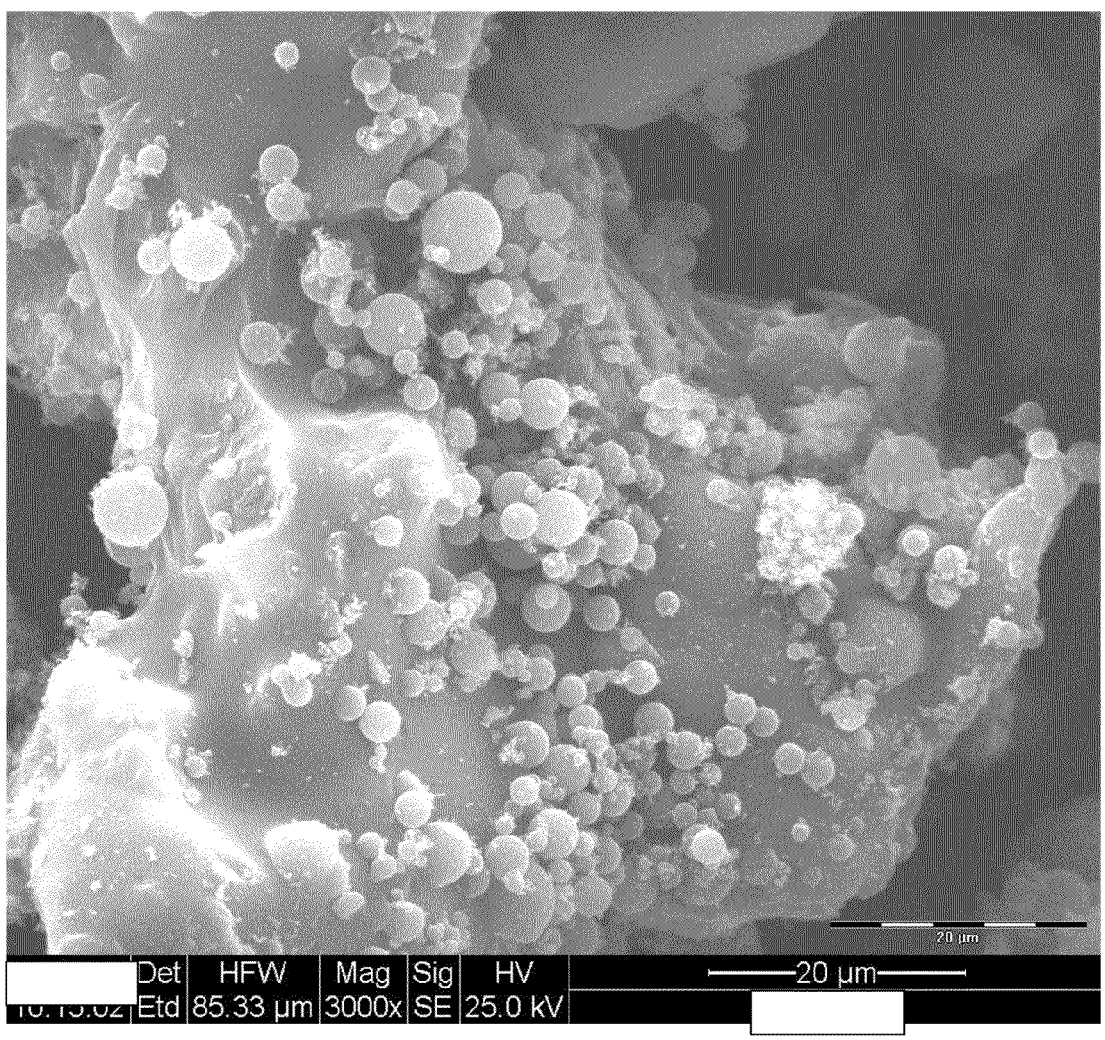

PROCESSES FOR COATING A CARRIER WITH MICROPARTICLES

CROSS-REFERENCE TO RELATED APPLICATIONS

This application claims the benefit of U.S. Provisional Patent Application Ser. No. 61/147,287, filed Jan. 26, 2009, which is incorporated herein by reference.

FIELD OF THE INVENTION

The present invention relates to processes for coating carriers with microparticles.

BACKGROUND OF THE INVENTION

Several processes for coating carriers with particles are known in the art. One typical process is performed by using a fluidized bed as the carrier. A fluidized bed is formed when a quantity of a solid particulate substance (usually present in a holding vessel) is placed under appropriate conditions to cause the solid/fluid mixture to behave as a fluid. This is usually achieved by the introduction of pressurized fluid through the particulate medium. This results in the medium then having many properties and characteristics of normal fluids.

According to one process known in the art, droplets of a suspension are sprayed on a fluidized bed, normally using a Wurster apparatus. The Wurster apparatus generally includes a container with a cylindrical partition extending upwardly therein, and with a perforated plate or screen at the lower end thereof to define a bottom wall for the particles. The partition is spaced above the perforated plate. The area within the cylindrical partition defines the upbed of the container, while the area outside the partition defines the downbed of the container. The perforated plate includes an area of large perforations and a greater percentage of perforated open area through which air flows into the upbed at an increased velocity, and an area of perforations with a lower percentage of open area through which air flows into the downbed at a decreased velocity. The higher velocity air in the upbed area transports the particles for coating, layering, and drying of a coating solution sprayed from a spray nozzle extending upwardly through the perforated plate and into the upbed area. The particles then encounter the lower velocity air in the expansion chamber above the partition. When the air velocity is insufficient to support the product, the particles fall into the downbed area for reentry into the higher velocity air, such that a cycle of coating in the upbed area and drying in the downbed area is achieved. Various forms of the Wurster apparatus and process are disclosed in U.S. Pat. Nos. 2,648,609, 2,799,241, 3,089,824, 3,196,827, 3,207,824, and 3,253,944.

In the pharmaceutical industry, an API (active pharmaceutical ingredient) is commonly introduced into the patient's body deposed on a carrier. Carriers are substances which are used to improve the performance of the dose form by increasing the uniformity of the blend and keep the API particles from aggregating. Many substances are known to be suitable as carriers in the pharmaceutical industry, for example: micro-crystalline cellulose, lactose and mannitol. Those skilled in the art generally choose a carrier based on its particle size distribution and solubility properties.

The Wurster apparatus method of coating results in carriers which are coated with a layer of API crystals with a large range of sizes. This layer is created due to the adherence of the droplets to the carrier particles prior to the evaporation of the solvent. In this method, the particles of API are suspended in a dispersion liquid. If the API particles are very small, they may aggregate and the suspension will not be uniform. In many cases, the API particles are not stable in the suspension, and the process should be performed soon after the creation of the suspension.

Furthermore, it may be readily understood that the Wurster apparatus method is not suitable for coating carrier particles with microdroplets of API solution or air-suspended dry microparticles because of the low probability of a microparticle or microdroplet to collide with a carrier particle. In this case, the microparticles might escape through the filtering system and the material will be lost.

Many efforts have been made to formulate suitable therapeutic agents as dry powders for delivery via inhalers. Typically, the formulations are produced by drying the active agent in the presence of certain excipients, such as polysaccharides or citrate, to enhance stability during the drying process or in storage.

CA-A-2136704 discloses a product obtained by spray-drying a medicinal substance such as insulin (among many others) and a carrier. WO-A-9735562 discloses spray-drying a solution of insulin and a polysaccharide. WO-A-9524183 is directed primarily to a dry powder that comprises insulin and a carrier material, typically a saccharide, in the form of an amorphous powder of microparticles obtained by spray-drying. WO95/23613 discloses a spray-dried DNase formulation. U.S. Pat. No. 6,926,908 discloses spray-dried therapeutic agent at high concentrations.

There is a need in the art for methods of coating carriers with microparticles of an API that are either suspended in air or formed from microdroplets.

BRIEF DESCRIPTION OF THE FIGURES

FIG. 1 is an SEM image of cellulose coated with nano-atomized API.

SUMMARY OF THE INVENTION

In one embodiment, the present invention provides a process comprising the steps of:
a. providing microdroplets of a solution of an API and a solvent;
b. evaporating the solvent from the microdroplets to obtain dry microparticles, and
c. contacting the microparticles with a static carrier bed or periodically agitated carrier bed to obtain a carrier coated with microparticles.

DETAILED DESCRIPTION OF THE INVENTION

The present invention encompasses processes for coating a static or periodically agitated carrier bed with microparticles.

In preferred embodiments the invention provides carriers coated with microparticles, wherein the microparticles can dissociate from the carrier.

The carriers which are obtained by the above process are coated by microparticles which are preferably generally round in shape and preferably have a relatively narrow range of sizes. Use of round microparticles is important, for example, in the inhalation pharmaceutical products industry since the relatively small, round particles flow more easily through the respiratory system and therefore the availability of the API is improved.

The round shape of the microparticle also provides minimal contact of the microparticle with the carrier, thus improving the ability of the API to separate from the carrier on which it is deposed and affecting the target site to a better extent.

Any API can be used in the practice of the present invention. Examples include docetaxel, other cytotoxic drugs, risperidone, beclomethasone, fluticasone, budesonide, other steroid drugs, salbutamol, terbutaline, ipratropium, oxitropium, formoterol, salmeterol, valsartan, ezetimibe, paliperidone, aprepitant, tacrolimus, sirolimus, everolimus and tiotropium.

As used herein "static carrier bed" is a layer of carrier particles such as lactose or micro-crystalline cellulose which is statically laid on a supporting mesh.

As used herein "periodically agitated carrier bed" is a static carrier bed that is periodically agitated by a suitable agitator to homogenize the powder and expose new carrier particles to the coating process.

As used herein "SEM" is Scanning-Electron Microscope, used to observe particles and structures in the micro-range. This microscope images the sample surface by scanning it with a high-energy beam of electrons in a raster scan pattern.

In a specific embodiment, the process of the present invention comprises the steps of:
 a. providing microdroplets of a solution of at least one API and a solvent;
 b. evaporating the solvent from the microdroplets to obtain microparticles, and
 c. contacting the microparticles with a static carrier bed or a periodically agitated carrier bed to obtain a carrier coated with microparticles.

Preferably, the microdroplets are obtained by an atomizer. An atomizer is an apparatus which creates a spray of small droplets from a liquid, solution or a suspension. Many types of atomizers are known, varying in the generated droplet size and mechanism of operation. Jet-atomizers create droplets by co-spraying them with a jet of air. Rotary disk atomizers create droplets by creating a layer of liquid on a rotating disc. Ultrasonic atomizers disperse the liquid into droplets by means of ultrasonic vibrations. Nano-atomizers create droplets by creating an ultra-thin layer of liquid on a membrane and spraying the atomization gas through the membrane, breaking the thin liquid layers to sub-micron droplets. Atomizers differ in performance and in parameters such as droplet size, droplet velocity, and droplet concentration in the carrier gas.

Several atomizers are available for the purpose of preparing the microdroplets, for example Ultra Sonic Atomizer (SonoteK, http://www.sonozap.com/Ultrasonic_Atomizer.html) and Nano-Sol nano-atomizer (http://www.nanosol-il.com/prods.html) which is described in U.S. Pat. No. 6,899,322. The atomizer makes use of a gas, typically nitrogen or $CO_2$ gas, as the spraying and conveying gas (the gas that generates the microdroplets and then carries them to the target) so that the microdroplets are released from the atomizer surrounded by gas.

The obtained microdroplets preferably have an average diameter of about 1-15 micrometers, preferably 1-3 micrometers. Preferably, the solution from which the microdroplets are obtained is a solution of an API which is completely dissolved in an appropriate solvent or surfactant. The ratio of API to solvent or surfactant preferably varies between about 1% to about 30% and one may adjust this ratio of API to solvent or surfactant to obtain microdroplets and particles at different sizes or different density. The solution may include other ingredients, such as additional API, preservatives, stabilizers, colorants, etc.

A preferred surfactant is selected from the group consisting of poly vinyl alcohol (PVA), polysorbate 80 (polyoxyethylene (20) sorbitan monooleate), polysorbate 20 (polyoxyethylene (20) sorbitan monolaurate), poloxamer 188, polyethoxylated 35 castor oil (cremophor EL), polyethoxylated 40 hydrogenated castor oil or a mixture thereof.

In order to direct the gas stream and microdroplets (or microparticles, if spontaneous evaporation has already taken place) flow, through a pipe, towards a vessel which contains the static carrier, vacuum is preferably applied to the downstream side of the carrier bed. The vacuum suction is preferably just high enough to overcome the pressure drop over the bed and provide laminar air flow. Preferably, the pipe is designed to enable the stream of gas and microdroplets/particles to flow in a laminar flow manner, thereby reducing to a minimum the amount of particles which adhere to the walls of the pipes and vessels.

Evaporation of the microdroplets to obtain microparticles may be achieved spontaneously due to the relatively large surface face of each microdroplet. It may also be achieved, for example, by heating the pipe through which the stream of gas and microdroplets pass through, towards the vessel which contains the static bed. Optionally, the vessel in which the carrier bed is situated may also be heated to assist evaporation. Typically, temperatures of about 40-100° C. along part of the pipe length will be sufficient to evaporate the solvent of the microdroplet.

Preferably, when reaching the vessel in which the static or periodically agitated carrier is situated, the solvent has already partially evaporated from the microdroplets to obtain moist microparticles; more preferably the solvent has already completely evaporated from the microdroplets to obtain dry microparticles. One skilled in the art would determine the appropriate evaporation conditions so that he may control the water content in the microparticle. In some cases, moist particles will allow better adhesion of the microparticles to the carrier.

Preferably the microparticles which are obtained are round in shape. This may be achieved at least in part by evaporating the solvent from the microdroplet prior to contact with the carrier. The dry microparticles preferably have an average diameter of about 100 nm to about 10,000 nm, preferably about 200-5,000, more preferably about 500-5,000 nm, most preferably about 500-1,000 nm.

Preferably the static carrier is an excipient which is known to be suitable in the pharmaceutical industry. Examples for suitable carriers are: microcrystalline cellulose (e.g., Avicel 101), lactose, and mannitol. Typically, the carrier is chosen according to the API which is deposited thereon and according to the route of administration. The particle size distribution of carrier particles may have an effect on efficiency of deposition and pressure drop across the bed. There are known methods to control and manipulate the size of carrier particles such as screening and milling.

Typically, the carrier is situated in the vessel on a mesh to ensure that the carrier particles do not escape from the vessel due to the vacuum. The mesh may be made of stainless steel, polyester, teflon, etc. One skilled in the art would choose the appropriate mesh having holes at a certain size according to the size of the carrier particles of interest, so that the mesh will enable the passage of the spraying and conveying gas without the escaping of carrier particles. For example, when using Avicel 101 it was found that the size of the holes is preferably between about 50 to about 100 microns.

The static carrier bed is typically agitated every 15 minutes using a stirrer to expose a new surface of the carrier to be coated by the dry microparticles. This serves to improve efficiency and consistency of the dry microparticles deposition.

Typically, once the gas stream and microdroplets/particles reach the vessel, the conveying gas (e.g., nitrogen) is readily removed from the vessel due to the vacuum through the spaces that are within the carrier bed and mesh. The dry microparticles, however, undergo deposition on the carrier since the carrier serves as a filter that prevents the microparticles from escaping out of the vessel.

In a preferred embodiment, the process is carried out in one stage. As used herein a "one stage process" refers to a process in which the microparticles are dried while it is being carried by a conveying gas to and coated onto the carrier. A process in which microparticles are dried then admixed with a carrier in a separate step, for example, would not be encompassed by the term "one stage process."

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. Absent statement to the contrary, any combination of the specific embodiments described above are consistent with and encompassed by the present invention.

EXAMPLES

The nano atomizer which was used in the examples is manufactured by NanoSol, utilizing 4 spraying elements. The experiments were performed using valsartan API. Polymorphs of valsartan have been described in WO 04083192A1 and processes for its preparation have been disclosed in WO 20040094391, both of which are incorporated herein by reference. It should be readily understood that the examples may apply for different APIs. The invention does not contain any inherent limitations on the choice of solvent and solute.

Example 1

Spray Coating of Cellulose with Valsartan API

A solution of 2% Valsartan in a solvent (ethanol) was sprayed by a nano atomizer to produce microdroplets having an average size of about 1-10 micrometers. Nitrogen gas was used as the spraying and conveying gas. The carrier was Avicel 101, screened by a 75 μm screen to remove fine particles. The purpose of the sieving was to decrease pressure drop over the bed. The bed collecting device was a modified filter-drier (model filterlab 80 by GL filtration LTD). The modification included a connection of a vacuum pump to the bottom of the vessel in order to remove the nitrogen and direct the flow of suspended particles and microdroplets to the bed. A second modification made to the instrument was removal of sintered metal filter media and replacing it with a supported mesh made of Polyester.

The piping connecting the atomizer and the collection vessel was designed to maintain laminar flow of the suspended particles and microdroplets. Therefore, deposition of particles on the piping walls was minimal. A heating element was installed in one segment of the pipe to assist evaporation of ethanol.

The pressure drop at the bed increased during the nano spray-coating. In about 20 minutes it rose from 30 mbar to 219 mbar. It was found that by agitating the bed, the pressure drop reverted back to its original value. In this example, 6 cycles were performed with total spraying time of 131 minutes.

Two samples were analyzed for valsartan content after different spraying times: one after 46 minutes and the other after 131 minutes. The samples were also observed by SEM.

From the SEM photos (see FIG. 1) it can be observed that the rounded shaped API particles (~100 nm-~10000 nm) were deposed on the carrier. From the assay analysis the API weight percentage (based on the total weight of API and carrier) was raised during the process: 4.21% after 46 minutes of spraying and 9.95% after 131 minutes.

What is claimed is:

1. A process comprising the steps of:
   (a) providing a conveying gas carrying microdroplets of a solution comprising an active pharmaceutical ingredient and a solvent;
   (b) evaporating the solvent from the microdroplets to obtain at least partially dried microparticles comprising the active pharmaceutical ingredient carried by the conveying gas;
   (c) contacting the at least partially dried microparticles comprising the active pharmaceutical ingredient carried by the conveying gas with a carrier bed to obtain a carrier coated with microparticles; and
   (d) applying a vacuum to the carrier bed to direct the conveying gas towards and across the carrier bed,
   wherein the carrier bed is a static carrier bed or a periodically agitated carrier bed.

2. The process of claim 1, wherein the active pharmaceutical ingredient is selected from the group consisting of: docetaxel, risperidone, beclomethasone, fluticasone, budesonide, salbutamol, terbutaline, ipratropium, oxitropium, formoterol, salmeterol, valsartan, ezetimibe, paliperidone, aprepitant, tacrolimus, sirolimus, everolimus and tiotropium.

3. The process of claim 1, wherein the carrier is selected from the group consisting of: microcrystalline cellulose, lactose, and mannitol.

4. The process of claim 1, wherein the microparticles have an average diameter of about 100 nm to about 10,000 nm.

5. The process of claim 4, wherein the microparticles have an average diameter of about 500 nm to about 5,000 nm.

6. The process of claim 5, wherein the microparticles have an average diameter of about 200 nm to about 5,000 nm.

7. The process of claim 6, wherein the microparticles have an average diameter of about 500 nm to about 1,000 nm.

8. The process of claim 1, wherein the solvent is ethanol.

9. A process comprising the steps of:
   (a) providing a conveying gas carrying microdroplets of a solution of an active pharmaceutical ingredient and a solvent;
   (b) evaporating the solvent from the microdroplets to obtain at least partially dried microparticles of the active pharmaceutical ingredient carried by the conveying gas;
   (c) coating a carrier with the at least partially dried microparticles of the active pharmaceutical ingredient carried by the conveying gas; and
   (d) applying a vacuum to direct the conveying gas towards and across the carrier.

10. The process of claim 9, wherein the carrier is selected from the group consisting of: microcrystalline cellulose, lactose, and mannitol.

11. The process of claim 9, wherein the microdroplets have an average diameter of about 1 to about 15 micrometers.

12. The process of claim 9, wherein the microparticles have an average diameter of about 100 nm to about 10,000 nm.

13. The process of claim 12, wherein the microparticles have an average diameter of about 500 nm to about 5,000 nm.

14. The process of claim 13, wherein the microparticles have an average diameter of about 200 nm to about 5,000 nm.

15. The process of claim 14, wherein the microparticles have an average diameter of about 500 nm to about 1,000 nm.

16. The process of claim 9, wherein the coating step comprises contacting the microparticles with a carrier bed to obtain a carrier coated with micro particles.

17. The process of claim 9, wherein the active pharmaceutical ingredient is selected from the group consisting of: docetaxel, risperidone, beclomethasone, fluticasone, budesonide, salbutamol, terbutaline, ipratropium, oxitropium, formoterol, salmeterol, valsartan, ezetimibe, paliperidone, aprepitant, tacrolimus, sirolimus, everolimus and tiotropium.

18. The process of claim 9, wherein the solvent is ethanol.

19. The process of claim 1, wherein the evaporating step comprises completely evaporating the solvent from the microparticles such that the microparticles are dry when coated on the carrier.

20. The process of claim 9, wherein the evaporating step comprises completely evaporating the solvent from the microparticles such that the microparticles are dry when coated on the carrier.

21. The process of claim 1, wherein the process is a one stage process.

22. The process of claim 9, wherein the process is a one stage process.

23. The process of claim 1, wherein step (d) comprises applying the vacuum to the down-stream side of the carrier bed to provide laminar flow to the conveying gas.

24. The process of claim 16, wherein step (d) comprises applying the vacuum to the down-stream side of the carrier bed to provide laminar flow to the conveying gas.

25. The process of claim 1, wherein the microdroplets have an average diameter of about 1 to about 15 micrometers.

* * * * *